US009671341B2

(12) United States Patent
Müller et al.

(10) Patent No.: US 9,671,341 B2
(45) Date of Patent: Jun. 6, 2017

(54) METHOD FOR THE OPERATION OF A LASER SCANNING MICROSCOPE

(71) Applicant: Carl Zeiss Microscopy GmbH, Jena (DE)

(72) Inventors: Martin Müller, Jena (DE); Nico Presser, Jena (DE); Gunter Möhler, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/795,491

(22) Filed: Jul. 9, 2015

(65) Prior Publication Data

US 2016/0011113 A1 Jan. 14, 2016

(30) Foreign Application Priority Data

Jul. 9, 2014 (DE) .................. 10 2014 010 185

(51) Int. Cl.
*G01N 21/64* (2006.01)
*G02B 21/00* (2006.01)
(52) U.S. Cl.
CPC ..... *G01N 21/6408* (2013.01); *G01N 21/6458* (2013.01); *G02B 21/008* (2013.01); *G02B 21/0032* (2013.01); *G02B 21/0076* (2013.01); *G01N 2201/067* (2013.01); *G01N 2201/0675* (2013.01); *G01N 2201/06113* (2013.01)
(58) Field of Classification Search
CPC ........... G01N 21/6408; G01N 21/6458; G02B 21/0032; G02B 21/0034; G02B 21/0076; G02B 21/008
See application file for complete search history.

(56) References Cited

U.S. PATENT DOCUMENTS

| | | | |
|---|---|---|---|
| 3,694,659 A | 9/1972 | Ramsay et al. | |
| 3,821,546 A | 6/1974 | McClenahan | |
| 4,367,404 A | 1/1983 | Kaye | |
| 4,563,707 A * | 1/1986 | Kishida | H01J 43/30 250/207 |
| 5,216,482 A * | 6/1993 | Fukui | G01N 21/63 356/313 |
| 2011/0149388 A1* | 6/2011 | Liedtke | G02B 21/008 359/385 |

(Continued)

FOREIGN PATENT DOCUMENTS

| | | |
|---|---|---|
| DE | 4105376 | 9/1991 |
| DE | 4417529 | 12/1994 |
| DE | 19702753 | 7/1998 |

(Continued)

*Primary Examiner* — Casey Bryant
(74) *Attorney, Agent, or Firm* — Haug Partners LLP

(57) ABSTRACT

Method for the operation of a laser scanning microscope. The microscope includes an illumination beam path in which at least one illumination light source is arranged, a detection beam path in which at least one photomultiplier (PMT) is incorporated as detector, and a control unit for controlling fluorescence experiments. A sample is alternately illuminated at high intensity via the control unit, and the fluorescence decay behavior of sample points and/or sample regions is subsequently detected. The PMT is switched on and off depending on the illumination mode by the control unit via a switch directly in the high-voltage supply of the PMT.

8 Claims, 4 Drawing Sheets

SCH: switch
A: control unit
S: signal line
K: photocathode layer
R: resistor
D: dynodes
MA: measurement output
e: photoelectron
P: photon

(56) References Cited

U.S. PATENT DOCUMENTS

2014/0138517 A1\* 5/2014 Liedtke .............. G02B 21/0076
   250/201.1
2016/0011113 A1\* 1/2016 Muller ............... G02B 21/0032
   250/459.1

FOREIGN PATENT DOCUMENTS

| DE | 10 2007 004 598 | 8/2008 |
| DE | 10 2009 060 309 | 6/2011 |
| WO | WO 83/02323 | 7/1983 |

\* cited by examiner

METHOD FOR THE OPERATION OF A LASER SCANNING MICROSCOPE

The present application claims priority from German Patent Application No. DE 10 2014 010 185.1 filed on Jul. 9, 2014, the disclosures of which are incorporated herein by reference in their entirety.

FIELD OF THE INVENTION

It is noted that citation or identification of any document in this application is not an admission that such document is available as prior art to the present invention.

Lasers of different power classes are used in a laser scanning microscope. Further, a laser scanning system is characterized by a large quantity of variable modules which serve as detector or for illumination.

A confocal scanning microscope contains a laser module which preferably comprises a plurality of laser radiation sources which generate illumination light of different wavelengths. A scanning device into which the illumination light is coupled as illumination beam has a main color splitter, an x-y scanner and a scanning objective for guiding the illumination beam by beam deflection over a sample located on a microscope stage of a microscope unit. A measurement light beam which is generated in this way and comes from the sample is directed to at least one confocal detection diaphragm (detection pinhole) of a detection channel via a main color splitter and imaging optics.

A beam path of a laser scanning microscope of this kind is shown schematically in FIG. 1. The light source, scanning module/detection unit and microscope are modules shown here. These modules will be described more fully in the following. Reference is also made to DE19702753A1 and the Zeiss laser scanning microscope LSM 710.

Lasers with different wavelengths are used in an LSM for specific excitation of different dyes in a specimen. The choice of excitation wavelength is governed by the absorption characteristics of the dyes to be examined. The excitation radiation is generated in the light source module. Different lasers (argon, argon-krypton, Ti:Sa lasers) are used for this purpose. Further, the selection of the wavelengths and the adjustment of the intensity of the required excitation wavelength, e.g., through the use of an acousto-optical crystal (AOTF), are carried out in the light source module. Subsequently, the laser radiation arrives in the scanning module via a fiber or a suitable mirror arrangement.

The laser radiation generated in the light source is focused in a diffraction-limited manner in the specimen by means of an objective via the scanner, scanning optics and tube lens. The focus point-scans the sample in x-y direction. The pixel dwell times while scanning over the sample are mostly in the range of less than one microsecond to several hundreds of microseconds.

During a confocal detection (descanned detection) of the fluorescent light, the light which is emitted from the focal plane (specimen) and from the planes above and below the latter reaches a dichroic beamsplitter (MD) via the scanner. This dichroic beamsplitter separates the fluorescent light from the excitation light. Subsequently, the fluorescent light is focused on a diaphragm (confocal diaphragm/pinhole) which is located exactly in a plane conjugate to the focal plane. Fluorescent light components outside of the focus are suppressed in this way. By varying the diaphragm size, the optical resolution of the microscope can be adjusted. Located behind the diaphragm is a further dichroic blocking filter (EF) which further suppresses the excitation radiation. After passing the blocking filter, the fluorescent light is measured by a point detector (PMT).

When multiphoton absorption is used, excitation of the dye fluorescence takes place in a small volume at which the excitation intensity is particularly high. This region is only negligibly larger than the detected region when using a confocal arrangement. Accordingly, a confocal diaphragm need not be used and detection can take place directly after the objective (non-descanned detection).

In a further arrangement for detecting a dye fluorescence excited through multiphoton absorption, a descanned detection is still carried out, but this time the pupil of the objective is imaged in the detection unit (non-confocal descanned detection).

Only that plane (optical slice) of a three-dimensionally illuminated image that is located in the focal plane of the objective is rendered through the two detection arrangements in connection with the corresponding single-photon or multiphoton absorption. By recording a plurality of optical slices in the x-y plane at different depths z of the sample, a three-dimensional image of the sample can be computer-generated subsequently.

The LSM is accordingly suitable for examining thick specimens. The excitation wavelengths are determined by the utilized dye with its specific absorption characteristics. Dichroic filters which are tuned to the emission characteristics of the dye ensure that only the fluorescent light emitted by the respective dye is measured by the point detector.

A central control unit A is connected to the most important microscope components via signal lines. For example, control of the utilized lasers and the intensity thereof is carried out via the acousto-optical filter (AOTF) downstream of the laser sources, and the detection and processing of the detection light is carried out via the connected PMTs in the partial detection beam paths depending on the detected scanner position and the resulting position of the illumination light on the sample for generating sample images.

In biomedical applications, a number of different cell regions are also labeled by different dyes simultaneously (multifluorescence). In the prior art, the individual dyes can be detected separately based either on different absorption characteristics or on emission characteristics (spectra). Further, an additional splitting of the fluorescent light of a plurality of dyes is carried out with the auxiliary beamsplitters (DBS), and a separate detection of the individual dye emissions is carried out in separate point detectors (PMT x).

A high sensitivity over a wide range is required for the PMT. The dynamics in many processes far exceed the range of compatibility of detectors. This is the case, for example, in FRAP experiments (see, e.g., the brochure for Zeiss LSM 710NLO, LSM 780NLO of March 2010). In this case, samples are observed in fluorescent light, i.e., very little light on the detector and, therefore, high gain through a very high voltage are necessary to obtain signals capable of being processed. In contrast, bleaching processes which influence the sample are initiated at short intervals through large amounts of light. Immediately thereafter, measurement is carried out again in fluorescence mode. For the bleaching process, the detector must be protected against excessive light to avoid destruction (blinding) or a long recovery time for the detector before the next measurement. This sequence is repeated very often. In order to protect the detector, a mechanical shutter may be inserted in front of the detector prior to the bleaching process or the high voltage is decreased to a low value through a control voltage. A protection of the detector is assured by these methods, but at approximately 0.5 s to 1 s, the waiting times between the switching processes are too long. A mechanical shutter requires additional installation space and incurs additional costs. This change often takes place several thousand times and accordingly leads to a productivity factor of a device. In order to conclude an extensive experiment within a short amount of time, the waiting period between the measurement process and the bleaching process should be reduced.

Heretofore, a controllable high-voltage generator was used, and this high-voltage generator must first be stepped down for experiments of this type. In some cases, this takes several hundreds of milliseconds. Stepping up the high-voltage generator again also takes one half of a second or longer. FIG. 2 shows an exemplary startup curve (U(t)) of a high-voltage generator of this kind when switched on. To protect the PMT, polarity reversal, short-circuiting and interruption of individual dynodes of the PMT (U.S. Pat. No. 3,821,546, U.S. Pat. No. 4,367,404, DE4105376, DE 102007004598, DE102009060309) or selective regulation of the high voltage depending on the anode signal (U.S. Pat. No. 3,694,659, DE3278295, DE4417529) are also often used. While this ensures fast protection of the anode, the cathode is not always sufficiently protected because there is still high voltage present at the dynodes or at the cathode during this time. Since the vacuum in the PMT is not an ideal vacuum, further light impinging on the dynodes and/or cathode can lead to ionization of the residual gas and accordingly allow the cathode to age, which is known in the art as ion feedback.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph), such that applicant(s) reserve the right to disclaim, and hereby disclose a disclaimer of, any previously described product, method of making the product, or process of using the product.

SUMMARY OF THE INVENTION

The problem to be solved by the invention consists in ensuring a maximum protection of the PMT in an economical manner with the briefest possible experiment duration in order to achieve a high repetition rate within the shortest amount of time, for example, in FRAP experiments.

BRIEF DESCRIPTION OF THE DRAWINGS

FIG. 2 shows an exemplary startup curve (U(t)) of a high-voltage generator of this kind when switched on.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

By incorporating a switch directly in the high-voltage line, much faster on/off switching times can be realized compared to direct modulation of the high-voltage source because the high-voltage source can be kept constant and is not changed. In addition, the photocathode of the PMTs can be comprehensively protected by means of the high-voltage switch in the high-voltage line because the high voltage is immediately interrupted. The ion feedback effect is accordingly reduced to a minimum. More cumbersome and slower solutions such as mechanical shutters can accordingly be dispensed with. Beyond this, the present invention lowers production costs and reduces the space requirement by doing away with the mechanical shutters in the LSM and allows faster and safer experiments for customers, e.g., FRAP experiments. There is also no need for modified PMT mounts from which the dynode contacts are guided out for switching. Accordingly, all existing PMTs can be used and no additional expenditures are needed.

In a particularly advantageous configuration, the actuation of the switch in the high-voltage line is timed directly by the control unit of the laser scanning microscope which, as has been stated, is also connected to all controllable microscope components such as illumination elements and detection elements. The timing is carried out in such a way that the high voltage is switched off [before] a bleaching process with high laser intensity and the high voltage is switched on again at the conclusion of the bleaching process or shortly thereafter so that, by means of the participating PMT, it corresponds to the above-mentioned fluorescence mode at low intensities of detection light.

Accordingly, in an advantageous manner, the PMT can be completely protected from the above-mentioned disadvantages and a series, e.g., a plurality of FRAP measurements, can nevertheless take place in quick succession.

To this end, a signal line is provided which connects the high-voltage switch to the control unit of the microscope which controls the utilized laser wavelengths and the intensity thereof.

The invention will be explained more fully in the following with reference to Illustrations 3 and 4.

Figure 3:
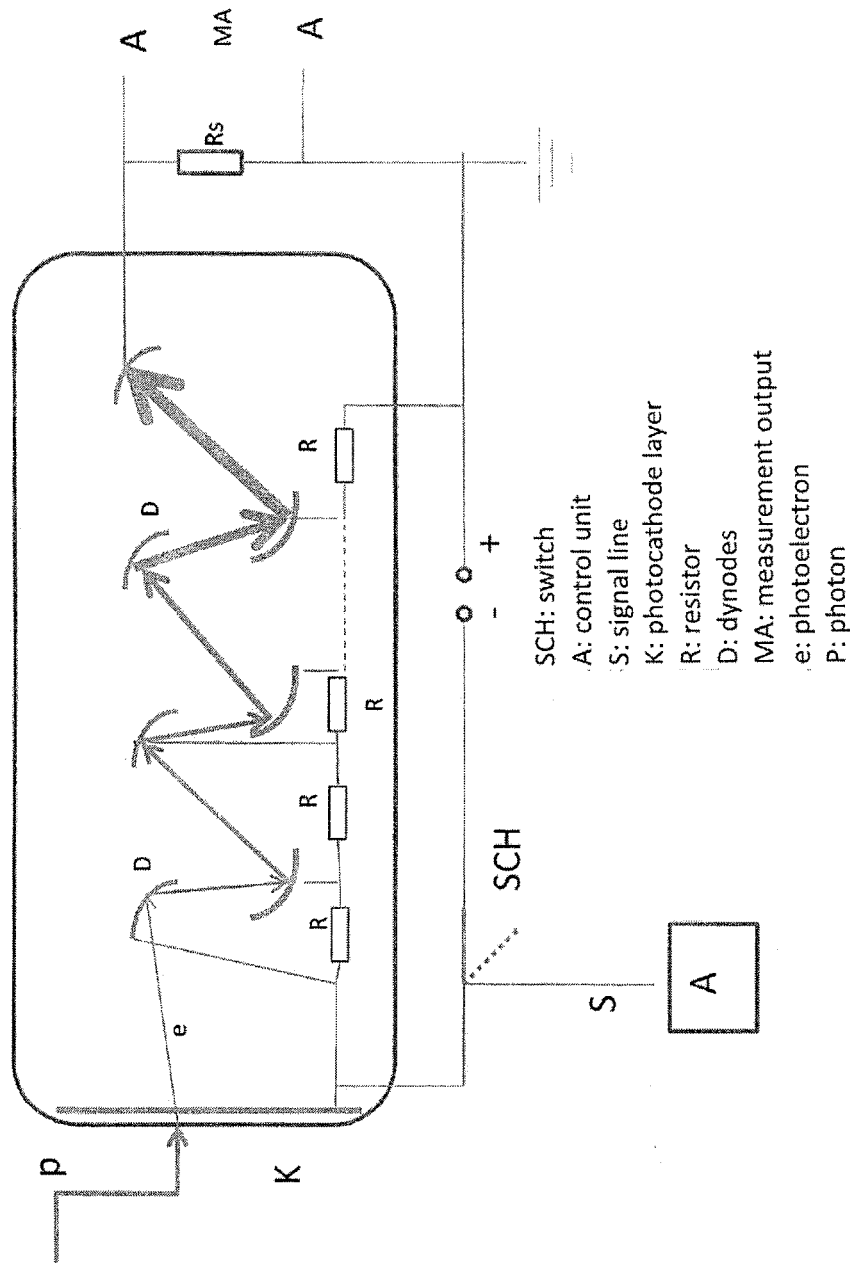
FIG. 3 shows a commonly used PMT.

FIG. 3 shows a commonly used PMT. The light photons p arrive on a cathode layer K and the photoelectrodes generated on the latter arrive in an amplified manner at the measurement output MA of the PMT via a plurality of dynodes D which are connected to a resistor cascade R.

Most commercial PMTs have only positive and negative terminals outside of their housing G for the applied high voltage for amplification via the dynode chain which is arranged inside the housing G and which is usually not accessible from the outside.

Figure 1:
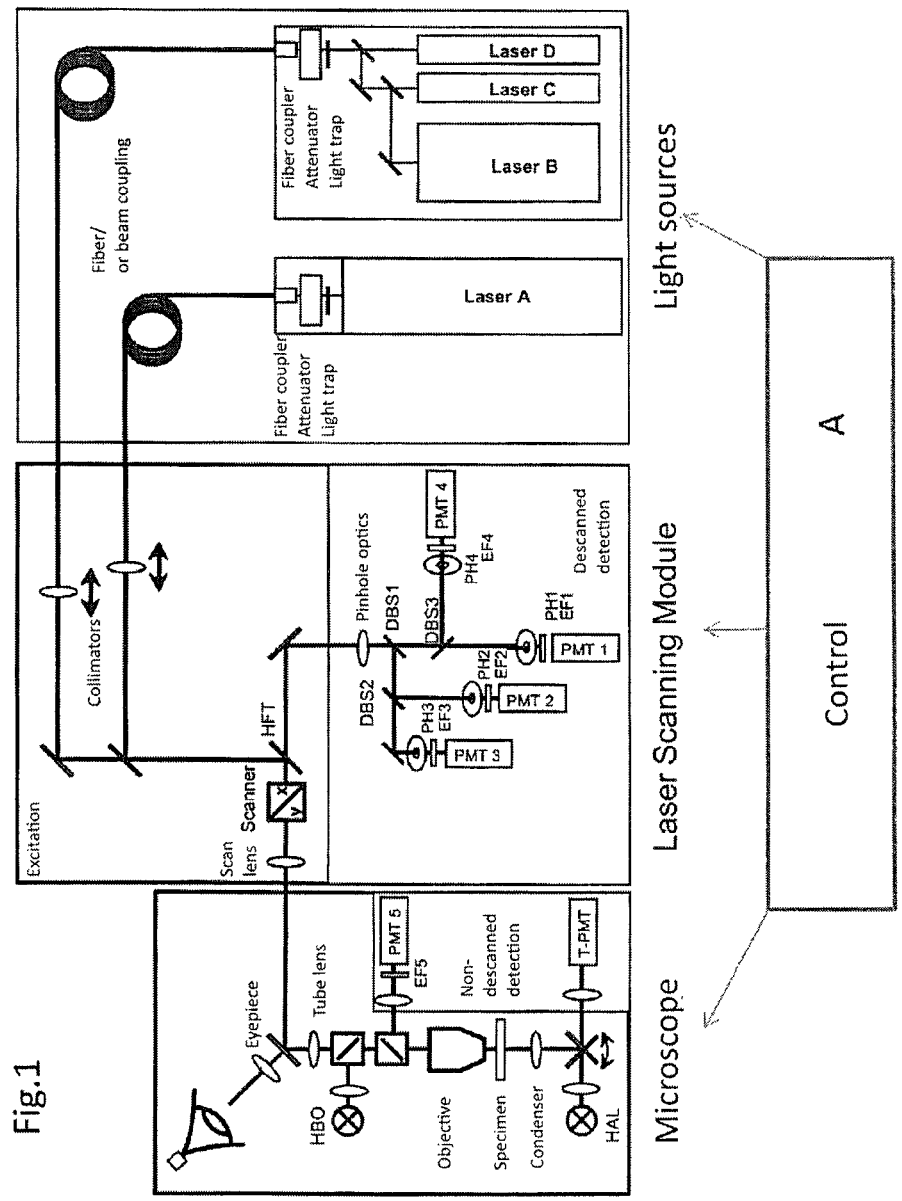
FIG. 1 schematically shows a beam path of a confocal laser scanning microscope.
Figure 2:
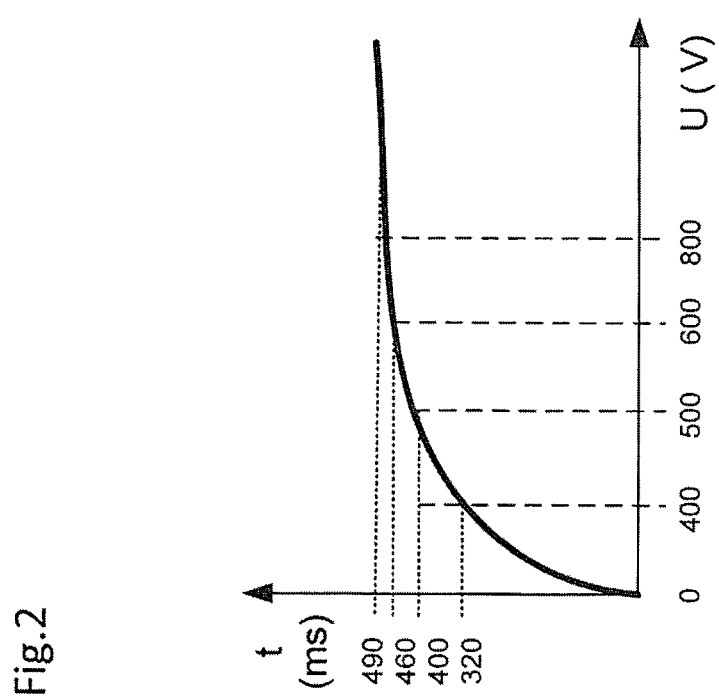

According to the invention, the advantageous on-off switch SCH is arranged in the high-voltage line, in this instance in the path leading to the cathode. The on-off switch SCH is connected to the control unit, shown in FIG. 1, of the utilized microscope via a signal line S, and this control unit can accordingly switch the high voltage on and off corresponding to the temporal situation of a measurement process of the microscope depending on the application of high-intensity laser light to the sample.

Figure 4A:
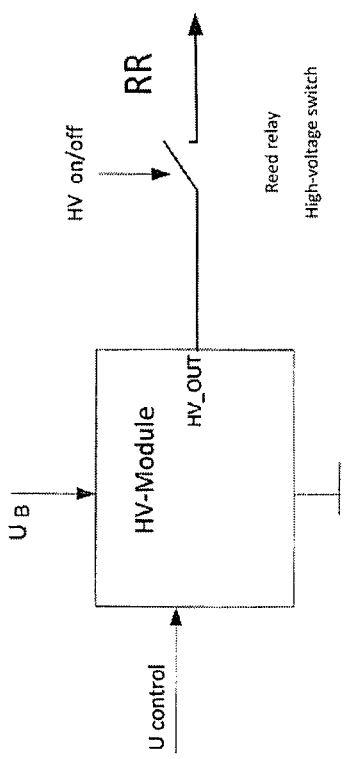
FIGS. 4a and 4b additionally show the high-voltage module HX which generates the applied high voltage.
Figure 4B:
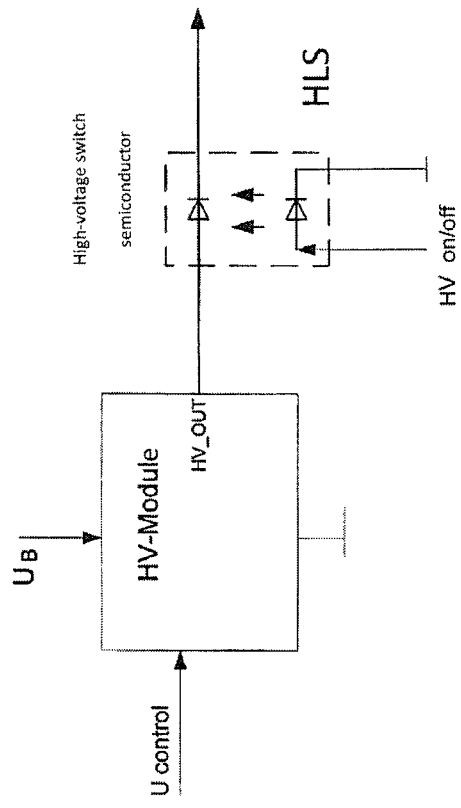

FIGS. 4a and 4b additionally show the high-voltage module HX which generates the applied high voltage.

In FIG. 4a, a high-voltage switch, for example, a reed relay RR, is provided at the output of HV high-voltage relay (e.g., GR2DNA by the firm Gigavac) in direction of the PMT (see FIG. 3).

In FIG. 4b, the switching function is realized by a semiconductor switch HLS that is suitable for high voltage (e.g., OC025 by the firm Voltage Multipliers).

The invention can advantageously be operative in all microscope systems using PMT detectors.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for the operation of a laser scanning microscope;
    wherein the laser scanning microscope comprises:
        an illumination beam path in which at least one illumination light source is arranged;
        a detection beam path in which at least one photomultiplier (PMT) is incorporated as detector; and
        a control unit configured to control fluorescence experiments by controlling utilized laser wavelengths and the intensity thereof;
    wherein the method comprises:
        alternately illuminating a sample while controlling utilized laser wavelengths and the intensity thereof via the control unit;
        subsequently detecting the fluorescence decay behavior of sample points and/or sample regions; and
        switching the PMT on and off depending on an illumination mode by the control unit via a switch in a high-voltage supply of the PMT, where the switch is arranged between a high-voltage module and the PMT so as to switch on and off high-voltage supply to a cathode layer and to a cascade of resistors, which are connected to a plurality of dynodes of said PMT.

2. The method according to claim 1,
    wherein switching the PMT on and off is carried out in synchronism with a change of illumination mode.

3. The method according to claim 2,
    wherein a switching off is carried out at the start of the high-intensity illumination; and
    wherein a switching on again is carried out when the illumination is switched off.

4. The method according to claim 1,
    wherein a switching off is carried out prior to, or at the start of the high-intensity illumination; and
    wherein a switching on again is carried out when, or after, the illumination is switched off.

5. A laser scanning microscope comprising:
    an illumination beam path in which at least one illumination light source is arranged;
    a detection beam path in which at least one photomultiplier (PMT) is incorporated as detector;
    a control unit; and
    an arrangement for high-voltage control of the PMT comprising:
        a high-voltage module configured to provide high-voltage to a cathode layer and a cascade of resistors which are connected to a plurality of dynodes of said PMT;
        a high-voltage supply line of the PMT for connecting said high-voltage module with said cathode layer and resistors; and
        an on-off switch arranged in the high-voltage supply line of the PMT, the on-off switch being configured switch the connection of said high-voltage module and the cathode layer and resistors on and off, respectively.

6. The laser scanning microscope according to claim 5;
    wherein said on-off switch is connected to the control unit via a signal line, and the control unit can accordingly switch the high voltage on and off corresponding to the temporal situation of a measurement process of the microscope depending on the application of laser light to the sample.

7. The laser scanning microscope according to claim 5;
    wherein the on-off switch is a high-voltage switch.

8. The laser scanning microscope according to claim 7;
    wherein the high-voltage switch is a reed relay or a semiconductor switch.

* * * * *